US00PP16011P2

(12) United States Plant Patent
Danziger

(10) Patent No.: US PP16,011 P2
(45) Date of Patent: Sep. 27, 2005

(54) ***TORENIA* PLANT NAMED 'DANTOPINKMN'**

(50) Latin Name: ***Torenia* sp.**
Varietal Denomination: Dantopinkmn

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 7 days.

(21) Appl. No.: 10/929,420

(22) Filed: Aug. 31, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,512 P * 9/2000 Danziger ..... Plt./263
PP11,784 P2 * 2/2001 Danziger ..... Plt./263
PP12,105 P2 * 9/2001 Miyazaki ..... Plt./263
2004/0128722 P1 * 7/2004 Iwaki ..... Plt./263
2004/0194181 P1 * 9/2004 Iwaki ..... Plt./263

OTHER PUBLICATIONS

UPOV ROM Computer Database, GTI Jouve Retrieval Software 2004/06 Citation(s) for 'Dantopinkmn'.*

* cited by examiner

*Primary Examiner*—Anne Marie Grunberg
*Assistant Examiner*—W. C. Haas
(74) *Attorney, Agent, or Firm*—Foley & Lardner, LLP

(57) ABSTRACT

A new and distinct *Torenia* plant named 'Dantopinkmn' particularly characterized by having shiny green foliage, doted with plenty of delicate, funnel form, cup shaped flowers in shades of pale and dark purple; bush, cascading, rounded and compact growth habit and densely branched; vigorous growth; early flowering, flowers all year round in moderate climate; suitable for use as an annual for hanging pots outdoors under partial shade; and good weather tolerance with preferred temperature range of 15–25° C.

2 Drawing Sheets

Botanical designation: *Torenia* sp.
Variety denomination: 'Dantopinkmn'.

BACKGROUND OF THE INVENTION

The present invention relates to a new and distinct cultivar of *Torenia* plant of the Scrophulariaceae family, hereinafter referred to by the cultivar name 'Dantopinkmn'.

The new cultivar originated in a controlled breeding program in Moshav Mishmar Hashiva, Israel. 'Dantopinkmn' was discovered and selected by the inventor, Gabriel Danziger, as an induced shoot mutation on a single flowering plant of the cultivar 'Dantopkmn', grown in a controlled, cultivated environment in Moshav Mishmar Hashiva Israel.

'Dantopinkmn' is an induced mutant of the cultivar *Torenia* 'Dantopkmn', commercially known as *Torenia* 'Pink Moon' (U.S. Plant Pat. No. 11,512), *Torenia* hybrid. The mutation arose by radiation, as a side shoot, stabilized by removing the cutting from the mutated sector of the treated plant.

Asexual reproduction of the new cultivar by soft tip cuttings was first performed in September, 2002 in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dantopinkmn' which in combination distinguish this *Torenia* as a new and distinct cultivar:

1. Shiny green foliage, dotted with plenty of delicate, funnel form, cup shaped flowers in shades of pale and dark purple;
2. Bush, cascading, rounded and compact growth habit and densely branched; vigorous growth;
3. Early flowering, flowers all year round in moderate climate;
4. Suitable for use as an annual for hanging pots outdoors under partial shade; and
5. Good weather tolerance with preferred temperature range of 15–25° C.

Of the many commercial cultivars known to the inventor, the most similar in comparison to 'Dantopinkmn' is *Torenia* 'Pink Moon' ('Dantopkmn'). Table 1 is a comparison of the two cultivars.

TABLE 1

| Characteristic | 'Dantopinkmn' | *Torenia* 'Pink Moon' ('Dantopkmn') |
|---|---|---|
| Flower color | Pale purple & dark purple | Pale purple & purple |
| Flower size (inches) (width by length) | 1.4 × 1.6 | 1.4 × 1.4 |
| Growth habit | Bush cascading | Cascading |
| Flowering time | 9 weeks from planting | 10 weeks from planting |

'Dantopinkmn' has not been observed under all possible environmental conditions. The phenotype of the new cultivar may vary with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

BRIEF DESCRIPTION OF THE DRAWING

The accompanying color photographs show typical flower and foliage characteristics of 'Dantopinkmn', with the colors being as true as possible with illustrations of this type.

The first photograph shows a flowering plant of 'Dantopinkmn' in its entirety.

The second photograph shows a close-up of 'Dantopinkmn'.

DETAILED BOTANICAL DESCRIPTION

The following observations, measurements and values describe the new cultivar as grown in Moshav Mishmar Hashiva, Israel, under conditions which closely approximate those generally used in commercial practice. For use as a pot plant, optimal growth conditions include growth outdoors in moderate climate, and indoors during winter. Irrigation and fertilization on a regular basis. The plant is usually grown in full sunlight, but partial shade is required in mid summer. Plants are fully grown in three months from planting a cutting, and bloom all year round in moderate climate. Color references are made to The Royal Horticultural Society Colour Chart (R.H.S.), except where general colors of ordinary significance are used. Color values were taken under daylight conditions at approximately noon in Moshav Mishmar Hashiva, Israel in June 2002. The age of the plant described is three months.

Propagation: Tissue culture propagation of young, in vitro plantlets and soft tip cuttings.

Plant:

*Form.*—Bush, cascading.

*Growth habit.*—Rounded and compact.

*Height.*—6 inches.

*Spread.*—20 inches.

*Blooming period.*—All year round in moderate climate.

*Cold tolerance.*—Frost tender; plants may be damaged by temperatures below 5° C.

*Vigor.*—Plants are fully grown in 3 months from planting a cutting.

Stem:

*Color.*—Yellow-Green RHS 146-B.

*Length.*—25 cm maximum length.

*Diameter.*—0.1 inch.

*Pubescence.*—Minimal; stem is quadrangular, hairs on the edges especially.

*Branching.*—About 20 main branches from the base that split into secondary and tertiary branches.

*Length of internodes.*—1.5 inches.

Foliage:

*Overall shape.*—Deltoid. Base: Cordate. Tip: Acuminate. Margin: Serrate.

*Color.*—Center color of leaf: Yellow-Green RHS 147-A. Upper side: Yellow-Green RHS 147-A. Under side: Yellow-Green RHS 146-A.

*Size of leaf.*—Width: 1.2 inches. Length: 1.7 inches.

*Petioles.*—Length, about 1.1 cm; Diametere, about 2 mm; Yellow-Green RHS 147-A.

*Leaf texture.*—Convex.

*Venation.*—Not prominent.

Flowers:

*Blooming period.*—Year round in moderate climate.

*Flowering stem.*—Flowers appear along the growing stems.

*Orientation at opening.*—Slanted upward.

*Type.*—Single.

*Shape.*—Funnel form.

*Petals.*—Size: 1.4 inches (width)×1.6 inches (length). Shape: Corolla tube cylindrical or often broadened above, 2-lipped, the upper lip faintly 2-lobed, the lower lip 3-lobed. Color: The upper lip pale purple, lower lip has purple blotches surrounding the corolla. Mature upper side: A mixture of RHS 76 D, RHS N 81 A, RHS N 80 B, RHS N 80 A. Mature under side: A mixture of RHS 76 D, RHS N 80 B, RHS N 80 C. Mature margin: A mixture of RHS 76 D, RHS N 81 A, RHS N 80 B. Mature throat: A mixture of RHS N 80 B. Immature upper side: A mixture of RHS 76 D, RHS 77 A and RHS N80A. Immature under side: A mixture of RHS 76 C, RHS N80 B and RHS N80 A. Immature margins: A mixture of RHS 76 D and RHS N81 A. Immature throat: RHS N 80 A.

*Peduncle.*—Length: 1.2 cm. Diameter: About 2 mm. Texture: Smooth. Color: Yellow-Green RHS 144-A.

*Bud.*—Shape: Oblong cylindrical ellipsoid 5 winged. Size: Length: 1 inch. Diameter: 0.4 inch. Color: RHS 144-A and RHS N 80 C.

Reproductive organs:

*Stamen.*—2 pairs; purple RHS 76 D.

*Style.*—Purple RHS 76 C in color; about 1.8 cm in length.

*Anther.*—Purple RHS 76 D in color; about 3 mm in length.

*Filament.*—Purple RHS 76 D.

*Ovaries.*—1, green RHS 143-A.

*Pollen color.*—RHS N155 C.

*Pistil.*—1 per flower; about 2.5 cm in length.

*Stigma.*—Shape: 2 lobes, deltoid. Color: RHS 76 B.

Seed/fruit: None.

Pest/disease resistance and/or susceptibility: A standard preventative spray program is sufficient as no susceptibility was observed.

I claim:

1. A new and distinct *Torenia* plant named 'Dantopinkmn', as illustrated and described herein.

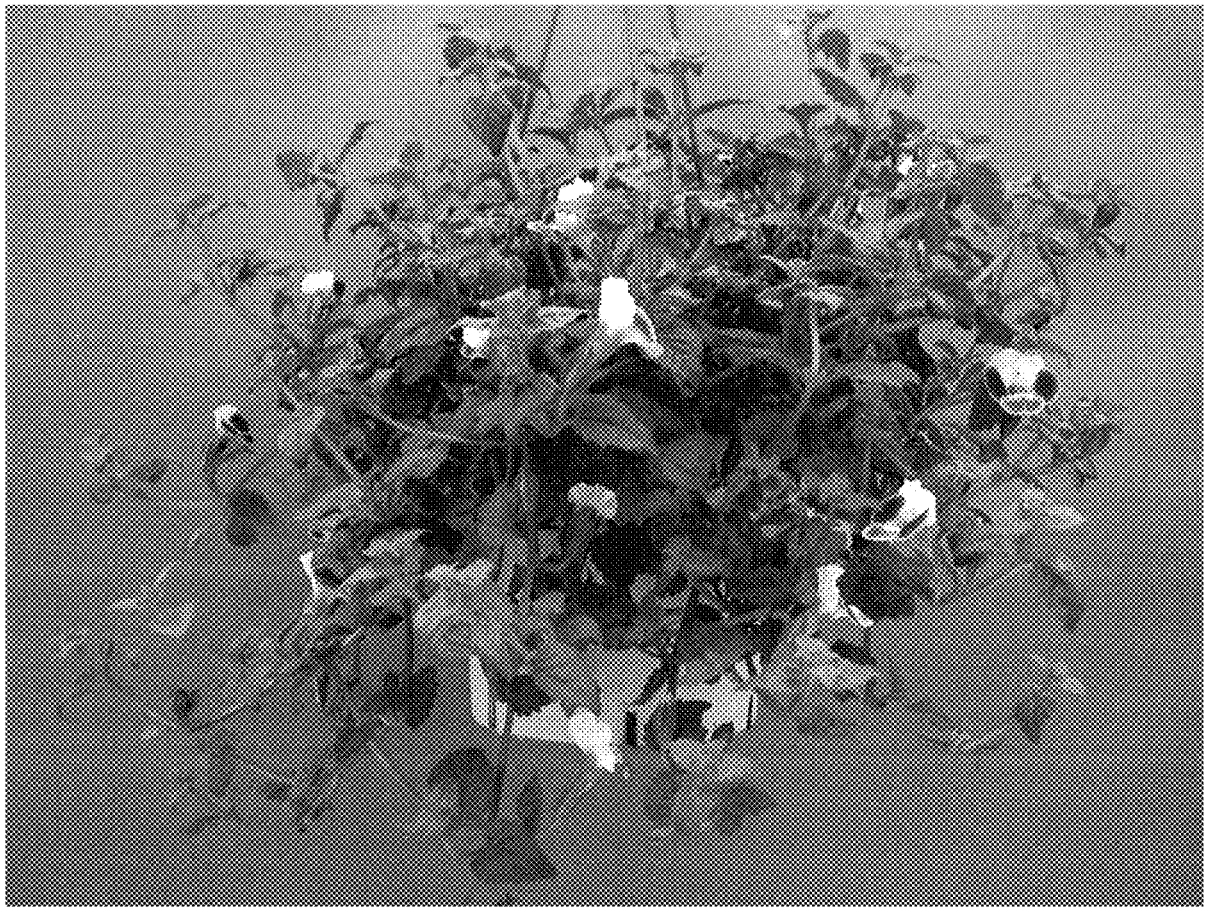

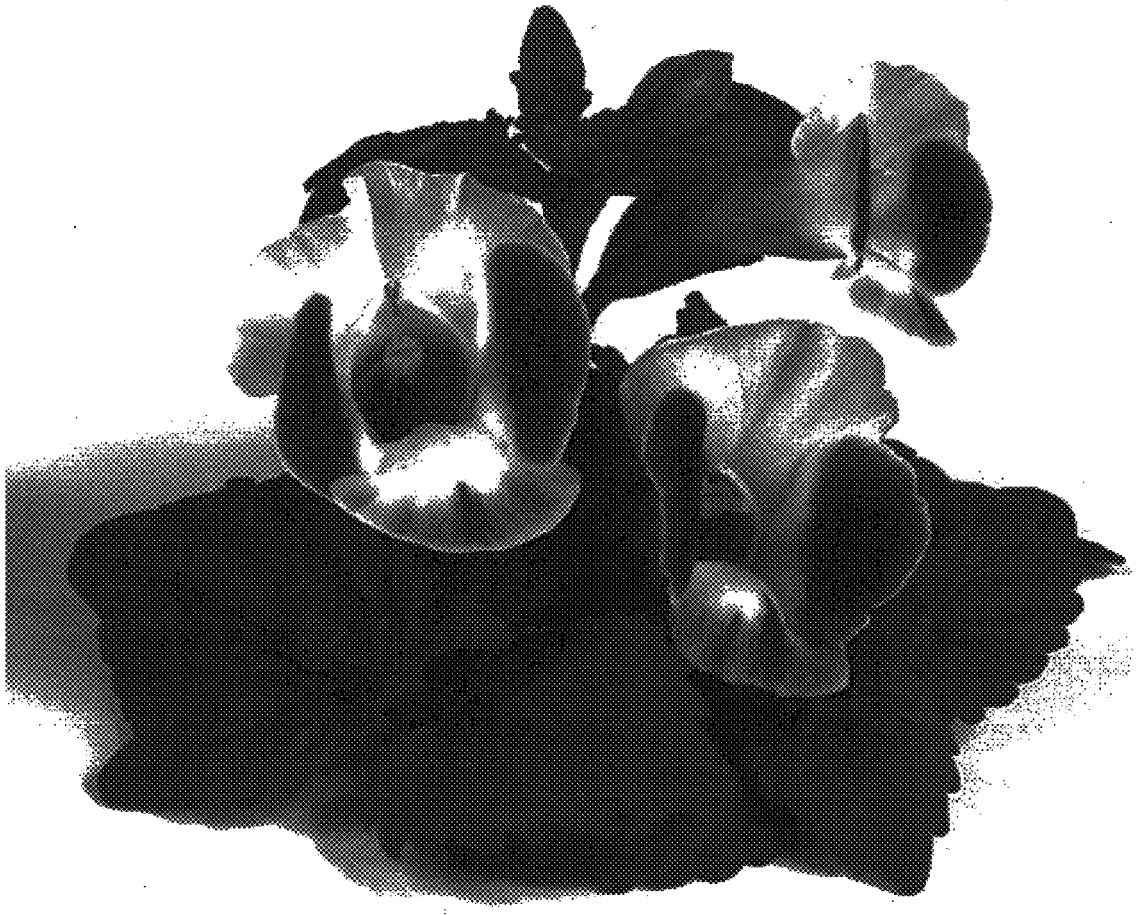

* * * * *